United States Patent
Danyluk et al.

(10) Patent No.: US 8,007,655 B2
(45) Date of Patent: Aug. 30, 2011

(54) METHOD AND APPARATUS FOR MEASURING PROPERTIES OF WEAK ELECTROLYTIC, ORGANIC FLUIDS SUCH AS HYDROCARBON-BASED FLUIDS

(75) Inventors: Steven Danyluk, Atlanta, GA (US); Francis Mess, Smyrna, GA (US); Sergey Tereshko, Atlanta, GA (US); Anatoly Zharin, Duluth, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 239 days.

(21) Appl. No.: 11/782,199

(22) Filed: Jul. 24, 2007

(65) Prior Publication Data

US 2009/0026090 A1    Jan. 29, 2009

(51) Int. Cl.
*G01N 27/416* (2006.01)
*G01N 27/26* (2006.01)

(52) U.S. Cl. ........ 205/775; 324/698; 324/425; 204/404; 205/777.5; 422/53

(58) Field of Classification Search .................. 204/404, 204/400; 205/793.5, 775.5, 776, 775, 777.5; 324/424–450, 698; 422/53
See application file for complete search history.

(56) References Cited

U.S. PATENT DOCUMENTS

| | | | |
|---|---|---|---|
| 2,752,566 A | | 6/1956 | Quinton |
| 3,645,669 A | * | 2/1972 | Rausch ........................ 8/137 |
| 3,763,007 A | * | 10/1973 | Seyl ............................ 204/404 |
| 3,876,916 A | | 4/1975 | Stoakes |
| 3,876,935 A | | 4/1975 | Guillermie et al. |
| 4,007,629 A | | 2/1977 | Hochstein |
| 4,029,554 A | | 6/1977 | Ellison |
| 4,506,337 A | | 3/1985 | Yasuhara |
| 4,646,070 A | | 2/1987 | Yasuhara et al. |
| 4,675,662 A | | 6/1987 | Kondo et al. |
| 4,677,847 A | | 7/1987 | Sawatari et al. |
| 4,701,713 A | | 10/1987 | Eaton et al. |
| 4,706,193 A | | 11/1987 | Imajo et al. |
| 4,733,556 A | | 3/1988 | Meitzler et al. |
| 4,741,204 A | | 5/1988 | Luck et al. |
| 4,744,870 A | | 5/1988 | Kauffman |
| 4,764,258 A | | 8/1988 | Kauffman |
| 4,796,204 A | | 1/1989 | Inoue |
| 5,023,133 A | | 6/1991 | Yodice et al. |
| 5,071,527 A | | 12/1991 | Kauffman |

(Continued)

OTHER PUBLICATIONS

Smiechowski, Matthew F., "Electrochemical Characterization of Lubricants for Microfabricated Sensor Applications", DRC Repository, 2005, 4 pages, OhioLINK Electronc Thesis and Dissertation Center, Case Western Reserve University ETDs, http://drc.ohiolink.edu/handle/2374.OX/16080.

(Continued)

*Primary Examiner* — Jeffrey T Barton
*Assistant Examiner* — Jennifer Dieterle
(74) *Attorney, Agent, or Firm* — Bryan W. Bockhop; Bockhop & Associates, LLC (57) ABSTRACT

A method and system for determining chemical properties of a fluid. The method and system include providing a weak electrolyte fluid, a container for the fluid, a detection method performed by a device having at least two electrodes, a detection and amplification device coupled to the electrodes and a sensed current compared to an uncontaminated, base fluid or compared to data characteristic of fluid contaminated or chemically changed in order to monitor and characterize the fluid.

5 Claims, 13 Drawing Sheets

U.S. PATENT DOCUMENTS

| | | | |
|---|---|---|---|
| 5,089,780 | A | 2/1992 | Megerle |
| 5,139,626 | A | 8/1992 | Yamaguchi et al. |
| 5,146,169 | A | 9/1992 | Morishita et al. |
| 5,262,732 | A | 11/1993 | Dickert et al. |
| 5,274,335 | A | 12/1993 | Wang et al. |
| 5,435,170 | A * | 7/1995 | Voelker et al. ............... 73/53.05 |
| 5,506,501 | A | 4/1996 | Fogel et al. |
| 5,518,590 | A | 5/1996 | Fang |
| 5,523,692 | A | 6/1996 | Kuroyanagi et al. |
| 5,604,441 | A | 2/1997 | Freese, V et al. |
| 5,644,239 | A | 7/1997 | Huang et al. |
| 5,750,887 | A | 5/1998 | Schricker |
| 5,754,055 | A | 5/1998 | McAdoo et al. |
| 5,789,665 | A | 8/1998 | Voelker et al. |
| 5,824,889 | A | 10/1998 | Park et al. |
| 5,929,754 | A | 7/1999 | Park et al. |
| 6,132,593 | A * | 10/2000 | Tan ............................ 205/776.5 |
| 6,217,745 | B1 | 4/2001 | Fang |
| 6,236,211 | B1 | 5/2001 | Wynn |
| 6,236,212 | B1 | 5/2001 | Wynn |
| 6,278,281 | B1 | 8/2001 | Bauer et al. |
| 6,286,363 | B1 | 9/2001 | Discenzo |
| 6,380,746 | B1 | 4/2002 | Polczynski et al. |
| 6,449,538 | B1 | 9/2002 | Kubo et al. |
| 6,549,015 | B2 | 4/2003 | Horie et al. |
| 6,551,479 | B1 | 4/2003 | Graham et al. |
| 6,577,112 | B2 | 6/2003 | Lvovich et al. |
| 6,590,402 | B2 | 7/2003 | Wang et al. |
| 6,598,464 | B1 | 7/2003 | Rossi |
| 6,644,095 | B2 | 11/2003 | Van Mullekom et al. |
| 6,718,819 | B2 | 4/2004 | Schoess |
| 6,791,334 | B2 | 9/2004 | Horie et al. |
| 6,799,458 | B2 | 10/2004 | Ismail et al. |
| 6,853,203 | B2 | 2/2005 | Beylich et al. |
| 6,859,039 | B2 | 2/2005 | Horie et al. |
| 6,867,603 | B2 | 3/2005 | Nicholson et al. |
| 7,019,654 | B2 | 3/2006 | Danyluk et al. |
| 7,038,459 | B2 | 5/2006 | Wakabayashi |
| 7,043,402 | B2 | 5/2006 | Phillips et al. |
| 7,043,967 | B2 | 5/2006 | Kauffman et al. |
| 7,266,472 | B2 | 9/2007 | Neumann et al. |
| 7,299,682 | B2 | 11/2007 | Boyle et al. |
| 7,391,225 | B1 * | 6/2008 | Lee et al. ....................... 324/698 |
| 2002/0113596 | A1 * | 8/2002 | Horie et al. ................... 324/438 |
| 2003/0112012 | A1 * | 6/2003 | Mosley et al. ................ 324/446 |
| 2005/0183969 | A1 * | 8/2005 | Luopa et al. ............... 205/775.5 |
| 2005/0241948 | A1 | 11/2005 | Han et al. |
| 2008/0066543 | A1 | 3/2008 | Sabini et al. |
| 2008/0068025 | A1 | 3/2008 | Gold et al. |

OTHER PUBLICATIONS

International Bureau of WIPO, "Notification Concerning Transmittal of International Preliminary Report on Patentability"; Feb. 4, 2010.

* cited by examiner

METHOD AND APPARATUS FOR MEASURING PROPERTIES OF WEAK ELECTROLYTIC, ORGANIC FLUIDS SUCH AS HYDROCARBON-BASED FLUIDS

The invention is directed generally to a method and system for property measurements of the chemistry changes in weak electrolytic, organic fluids, such as oils and other industrial fluids used in engineering systems. More particularly, the invention is directed to a method, system and apparatus for monitoring changes in the chemistry (degradation and contamination) of weak electrolytic fluids, such as hydrocarbon-based lubricants and oils for use in machines and motors as well as manufacturing and operating systems.

BACKGROUND OF THE INVENTION

Numerous machines and systems, such as automobile engines and machines used in manufacturing and processing operations rely on use of lubricants and oils for carrying out proper function. Lubricants and oils generally behave like weak electrolytes; and as a result their electrical properties can be measured, and changes in electrical properties can reflect changes in chemistry. Conventional systems do not monitor the actual properties of the fluid being employed while the systems are in operation. Typically, the fluids are either routinely changed at preset intervals or samples of the fluids are extracted, sent for chemical analysis; and depending on the outcome, the fluids are changed. While such an approach is generally acceptable, this prior art methodology results in (1) premature fluid change which is very wasteful and costly and (2) delayed fluid changes which can culminate in disastrous results and at least cause low efficiency operation or unnecessary damage to a motor, machine or system. Some monitoring systems do exist but are of low sensitivity or too expensive to use.

SUMMARY OF THE INVENTION

The properties of weak, electrolytic organic fluids can be measured and monitored by the system and method described herein. This system and method has broad applications for any method or system which requires production, processing or use of a weakly-electrolytic fluid of well defined chemical properties or use of a fluid with prescribed chemical properties with lack of contaminants for applications such as industrial operations and manufacturing. Such systems and methods include, without limitation, engines, transmissions, manufacturing operations and systems, and chemical plants and fluid-based processing systems.

The method and system can readily be applied to a measurement of electrolytic properties of hydrocarbon-based and other dielectric-based fluids. As an example, mineral oil, a hydrocarbon, is generally considered to be a dielectric. However, the method and system of the invention relates to the incorporation of additives, contamination or chemical degradation in the mineral oil to produce a weak electrolyte which is susceptible to characterization. The method and system detects electrical potentials and currents created in electrode pairs that are immersed in an electrolytic fluid, such as a hydrocarbon-based fluid. This method and system enables highly sensitive measurements in very short time periods of any change in additives, chemical degradation or contamination of a base line fluid being used, manufactured or processed in a system.

These and other objects, advantages, and features of the invention, together with the organization and manner of operation thereof, will become apparent from the following detailed description when taken in conjunction with the accompanying drawings, wherein like elements have like numerals throughout the several drawings described below.

DETAILED DESCRIPTION OF PREFERRED EMBODIMENTS

Figure 1:
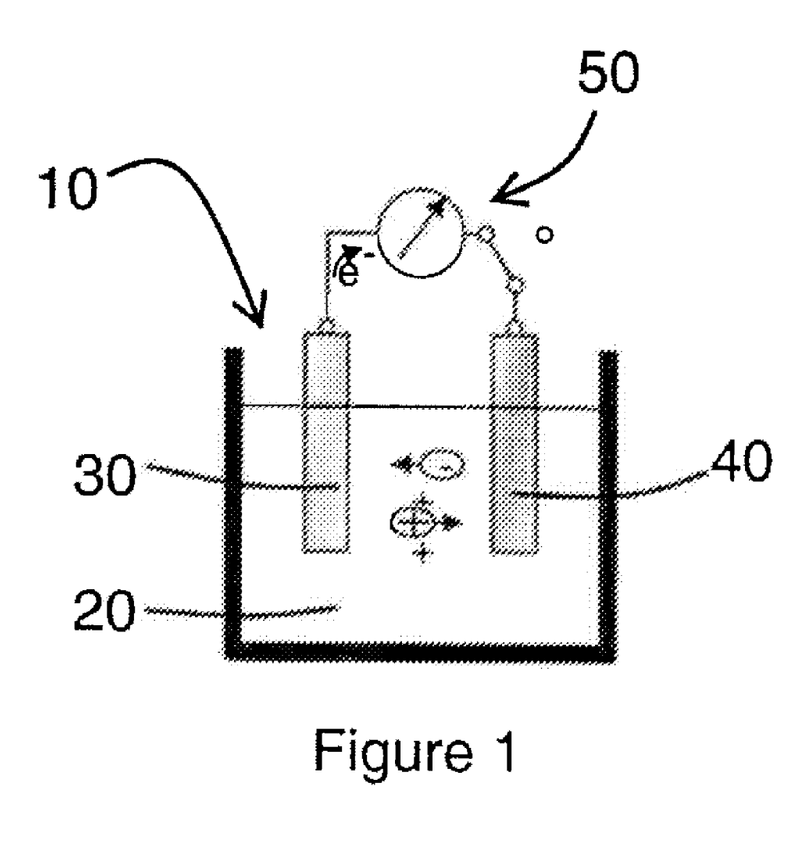
FIG. 1 is a schematic illustration of a measurement apparatus for a Galvanic potential or an electrolytic current.
Figure 2A:
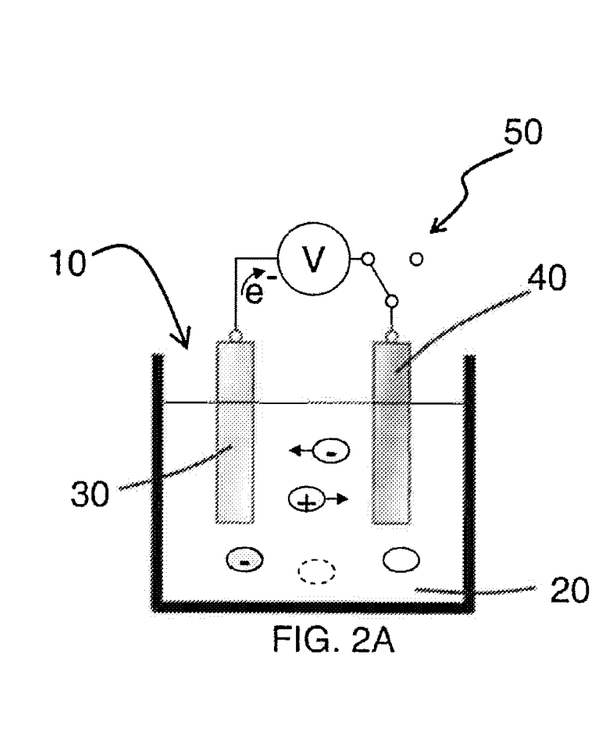
FIG. 2A is a schematic illustration of a Galvanic potential measurement apparatus.
Figure 2B:
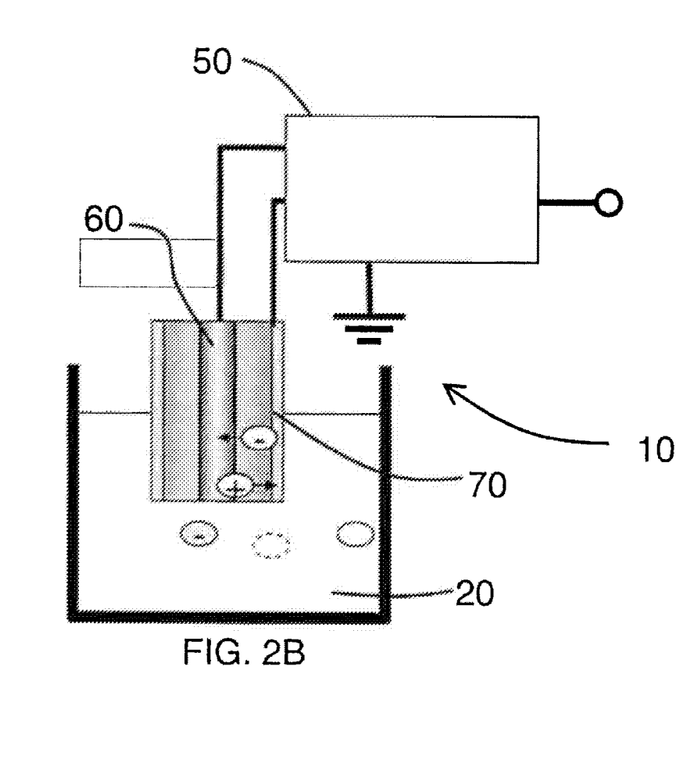
FIG. 2B shows a particular form of the embodiment of FIG. 2A.

In one form of the invention shown in FIG. 1, a detection apparatus 10 operates to measure electrolytic properties of a fluid 20, such as a hydrocarbon fluid disposed in a fluid container 25 shown schematically in FIGS. 2A and 2B. This container 25 represents any container device within which chemical properties of the fluid 20 can be measured. The apparatus 10 is comprised of two or more electrodes 30 and 40 which are coupled to a detection and amplification circuit device 50 such as an ammeter or a potentiometer with high input impedance. The electrodes 30 and 40 develop a Galvanic potential when electrically connected which causes an electrolytic current in the fluid 20. This electrolytic current is then detected by the device 50; and this current can then be analyzed for fluid property characteristics as will be described in more detail hereinafter.

Using the device 10 and the methods of the invention, a variety of exemplary measurements have been performed including, measurement of Galvanic potential by using very high impedance DC techniques, measurement of corrosion currents by use of low-impedance DC techniques, low frequency applied voltage bias modulation and measurement of electrolytic current and induced current and the use of closed-loop feedback methods to apply and measure the potential required to cancel, or nullify, the Galvanic potential and electrolytic current between the electrodes 30 and 40.

Figure 3:
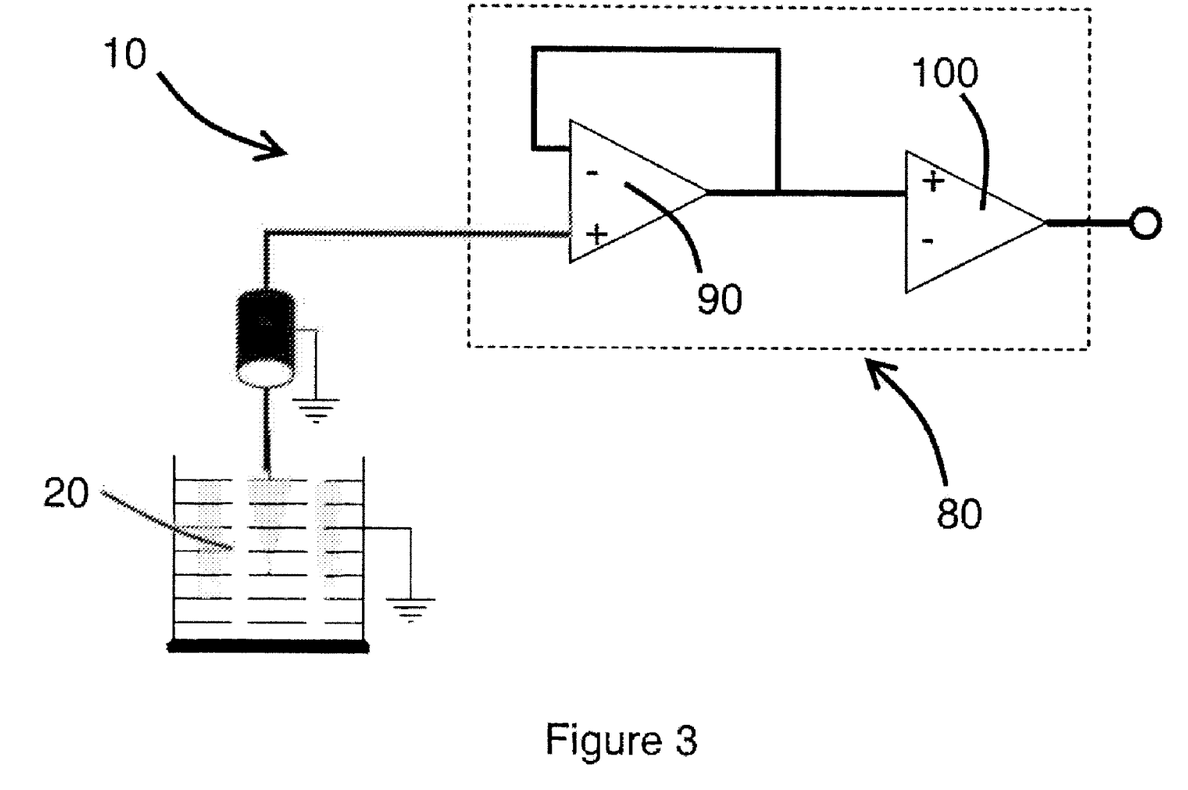
FIG. 3 is a schematic diagram of an electronic circuit for Galvanic potential detection and signal amplification.
Figure 6:
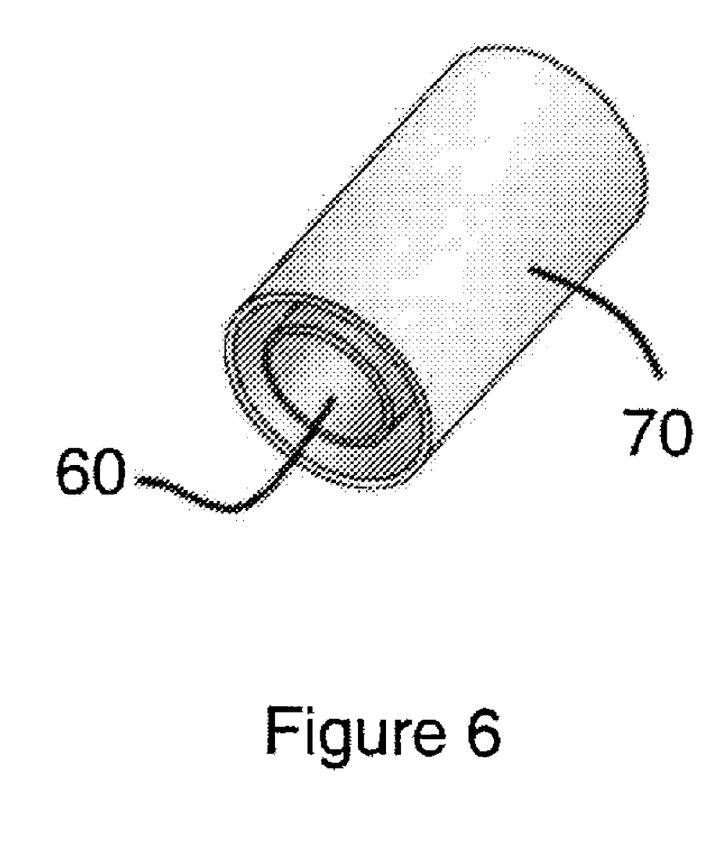
FIG. 6 is a perspective view of an electrode arrangement of concentric metallic tube electrode pairs for implementing potential and current measurements.

In a preferred embodiment of the invention, the device 10 is shown in FIGS. 2A and 2B in which the two electrodes 30 and 40 are configured as concentric cylinders 60 and 70 (see detail in FIGS. 2B and 6). A Galvanic potential will develop between the electrodes 30 and 40 (or 60 and 70), and that potential is related to the particular material characteristics of the pair of the electrodes 30 and 40 (or 60 and 70) and also the properties of the fluid 20. This potential can be measured by a detection circuit 80 shown in FIG. 3. The circuit 80 preferably includes a high impedance pre-amplifier 90 and a gain and buffer power amplifier 100.

In preferred embodiments of the invention a variety of methodologies can be performed, including measurement of corrosion currents by low-impedance DC measurements, low-frequency applied bias modulation and measurements of electrolytic currents as well as induced current and the use of closed loop feedback to apply and measure the electrical potential required to nullify the Galvanic potential and electrolytic current between the electrodes 30 (60) and 40 (70).

Figure 4A:
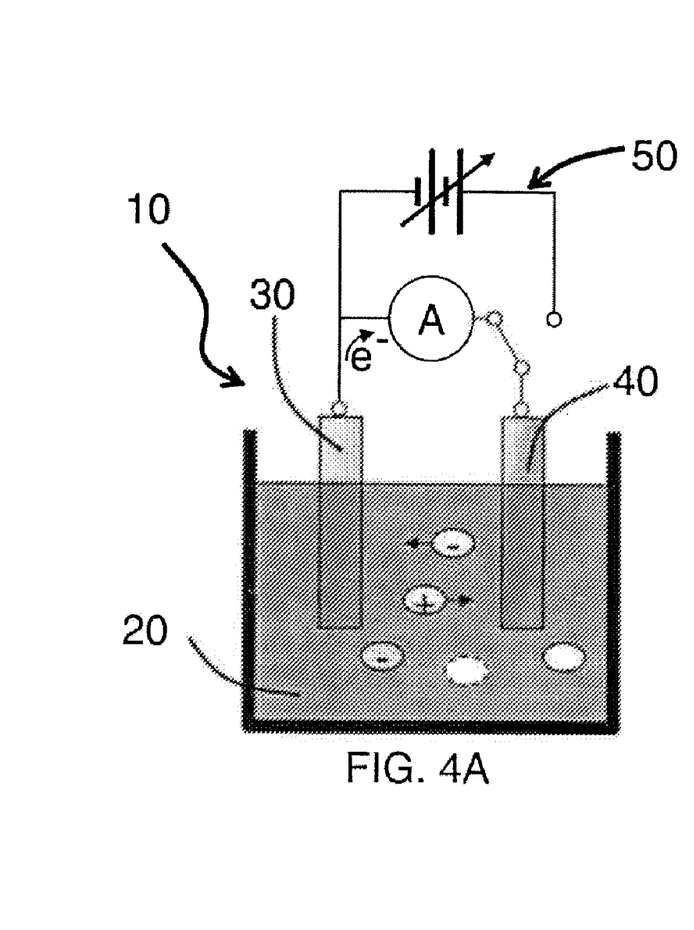
FIG. 4A is a schematic illustration of a current measurement apparatus.
Figure 4B:
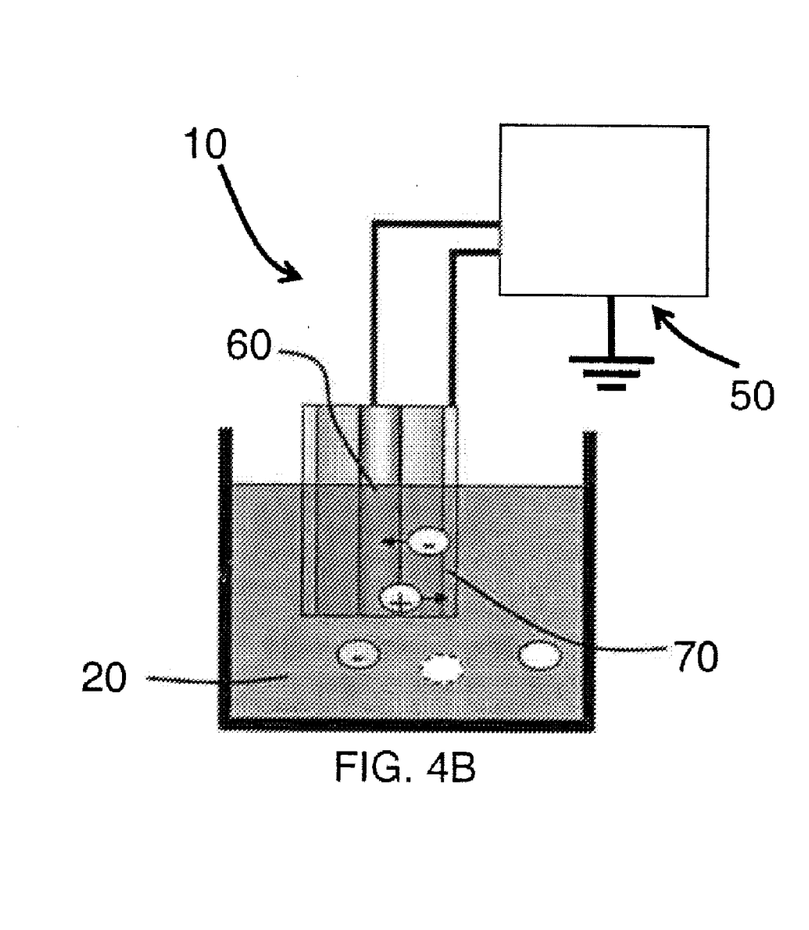
FIG. 4B shows a particular form of the embodiment of FIG. 4A.
Figure 5:
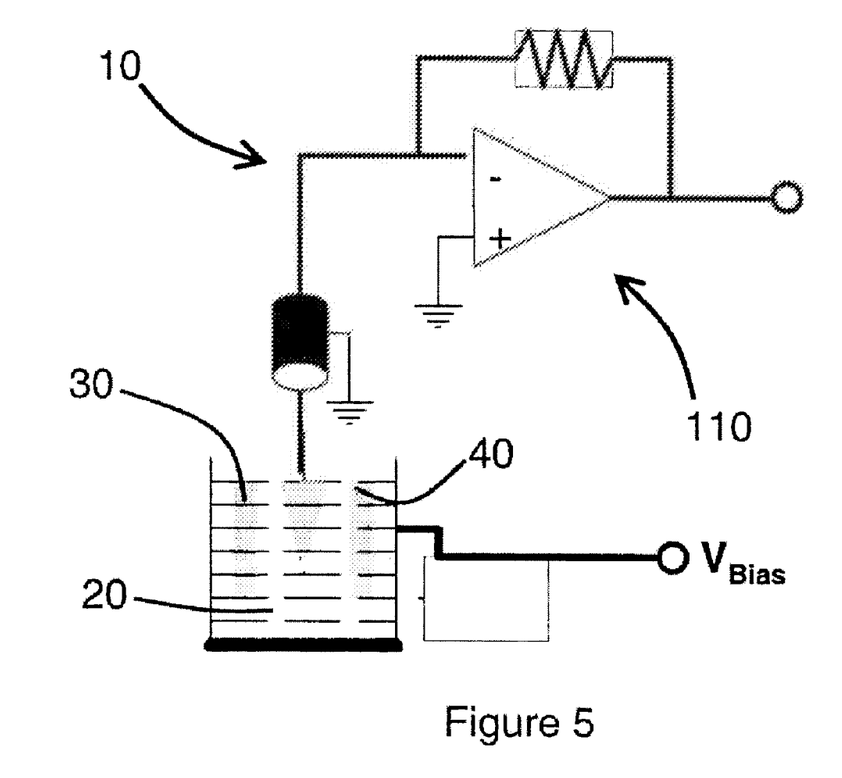
FIG. 5 is a schematic diagram of a current detection and amplification circuit.

The electrical circuit system 110 shown in FIG. 5 can be used to carry out these measurements. As shown in FIGS. 4A and 4B in the system 110, an electrolytic current develops between the electrodes 30 and 40 (or 60 and 70 in FIGS. 2B and 4B) that is driven by the Galvanic potential of the particular electrode pair and the properties of the fluid 20. This current flows through the bulk of the electrolyte as well as through the space charge layers associated with the surfaces of the electrodes. This current can be measured when zero bias is applied to the electrodes 30 and 40 (or 60 and 70), and is related to the electrolytic properties of the fluid 20. Alternatively or in combination with the above technique, a time-varying bias can be applied to the electrodes 30 and 40 (or 60 and 70), and the current can be measured. The current thus induced has both DC and transient signal components that are related to the electrolytic properties of the fluid and especially of the space charge regions 20. Alternatively or in combination with the above techniques, the magnitude of the applied bias can be controlled using closed-loop feedback to equilibrate the potential between the electrodes 30 and 40 (or 60 and 70), thereby nullifying the Galvanic potential, and/or the electrolytic current. By measuring changes in the applied bias required to nullify the potential and/or current, changes in the electrolytic properties of the fluid 20 can be detected since the composition of the space charge regions will depend on the chemistry of the additives in the hydrocarbon fluid. This approach has the additional benefit of reducing the rate of corrosion of the electrodes 30 and 40 (or 60 and 70), thus extending the service life of the electrode pair.

In all cases, the signal or data output that is developed by use of the device 50 (in FIG. 4B or the counterparts such as 110 in FIG. 5 in other embodiments) is related to the specific design and structure of the electronics, to the metallurgy of the electrode pair, and to the electrolytic properties of the fluid 20 being measured. Changes in fluid properties lead to a change in measured signal by virtue of the advantageous high level of sensitivity to any changes.

Figure 7:
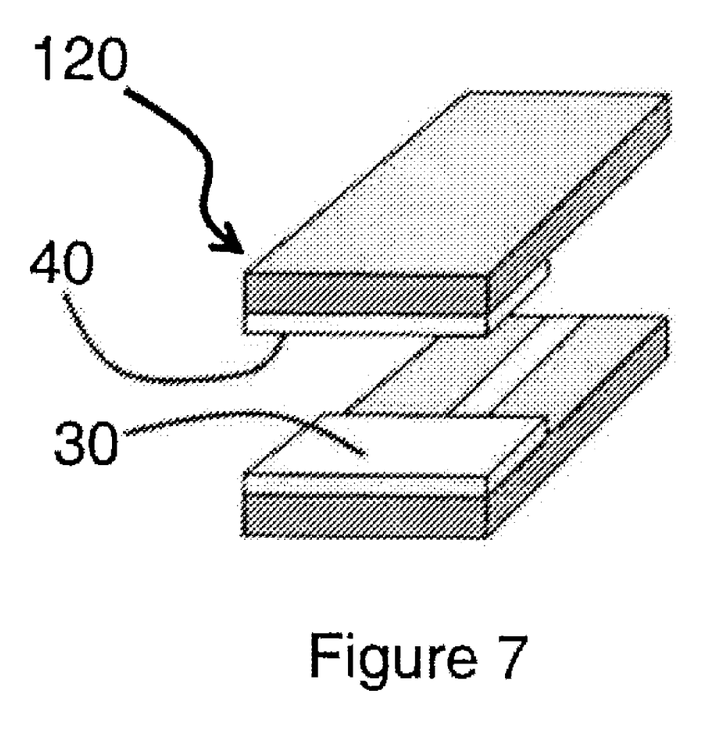
FIG. 7 is a perspective view of an electrode arrangement in the form of a non-conductive printed circuit board having the electrodes as patterned metallic electrodes in parallel.

In yet another form of the invention the electrodes 30 and 40 (or 60 and 70) can be structured to be part of a printed circuit board device 120 shown in FIG. 7. The measurements arising from changing fluid composition, additives, chemical state or contaminants can be processed in the same manner as for the device 10 described hereinbefore. More details of the measurement technique are illustrated by reference to FIG. 9A-9C which shows the origin of the total current measured (the sum of space charges one and two and the DC component). In FIG. 9B there is shown schematically space charge layers 130 at the interface between the fluid 20 and the electrodes 30 and 40 (or 66 and 70). In the circuit 135 shown in FIG. 9C, a space charge current developed across each of the circuit elements 140 and 150 and the direct circuit in circuit element 160. As shown in FIGS. 4A and 4B, when an external DC bias is applied to the circuit 135 in FIG. 9C, the measured current response is ohmic in nature and limited by the bulk resistivity of the fluid 20. The transient and DC current that exists when the external DC bias is removed or modulated results in a measured useful current for characterization of the fluid 20. This measured current is limited by the space charge region, and this above described method effectively removes the ohmic contribution from the measured signal.

The following non-limiting examples illustrate certain aspects of the invention.

Example 1

Figure 8:
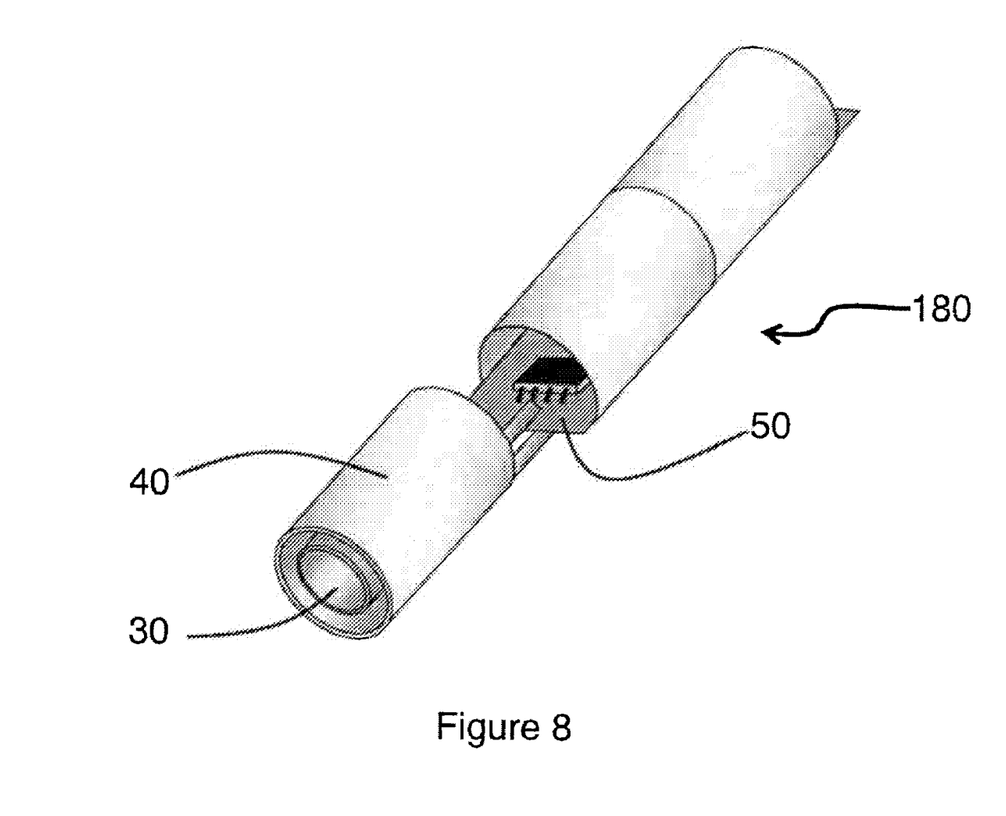
FIG. 8 illustrates one form of sensor for implementing measurement of fluid properties in accordance with the invention.
Figure 9A:
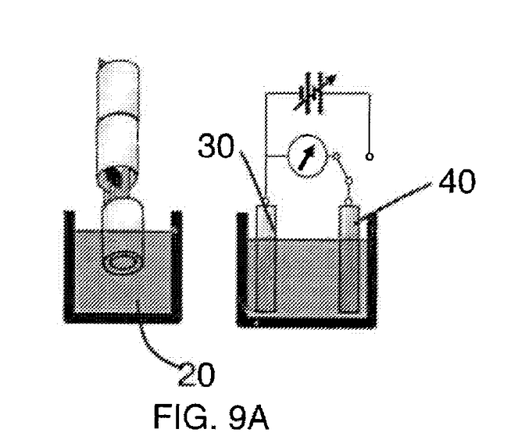
FIG. 9A illustrates basic operation and measurement by the system and method of one embodiment.
Figure 9B:
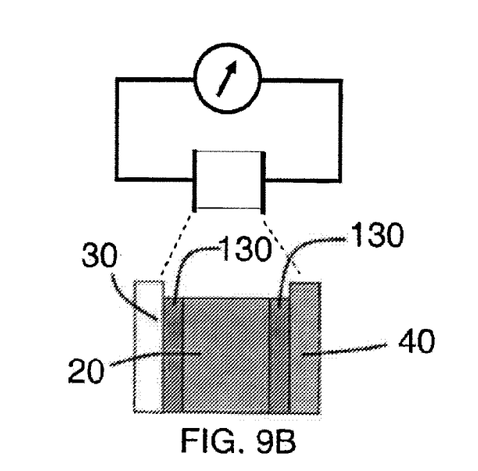
FIG. 9B shows development of space charge layers at the fluid-electrode interface and FIG. 9C shows the measured electrical circuit for measurement of the two space charge currents and direct current.
Figure 9C:
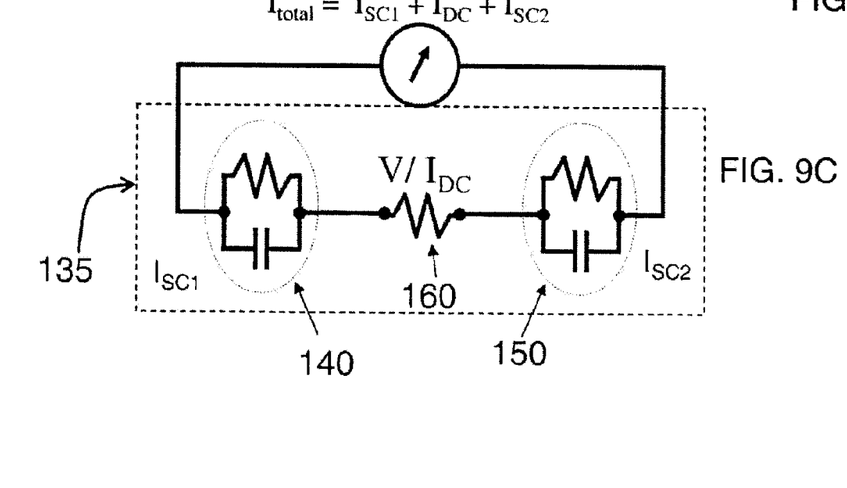
Figure 10:
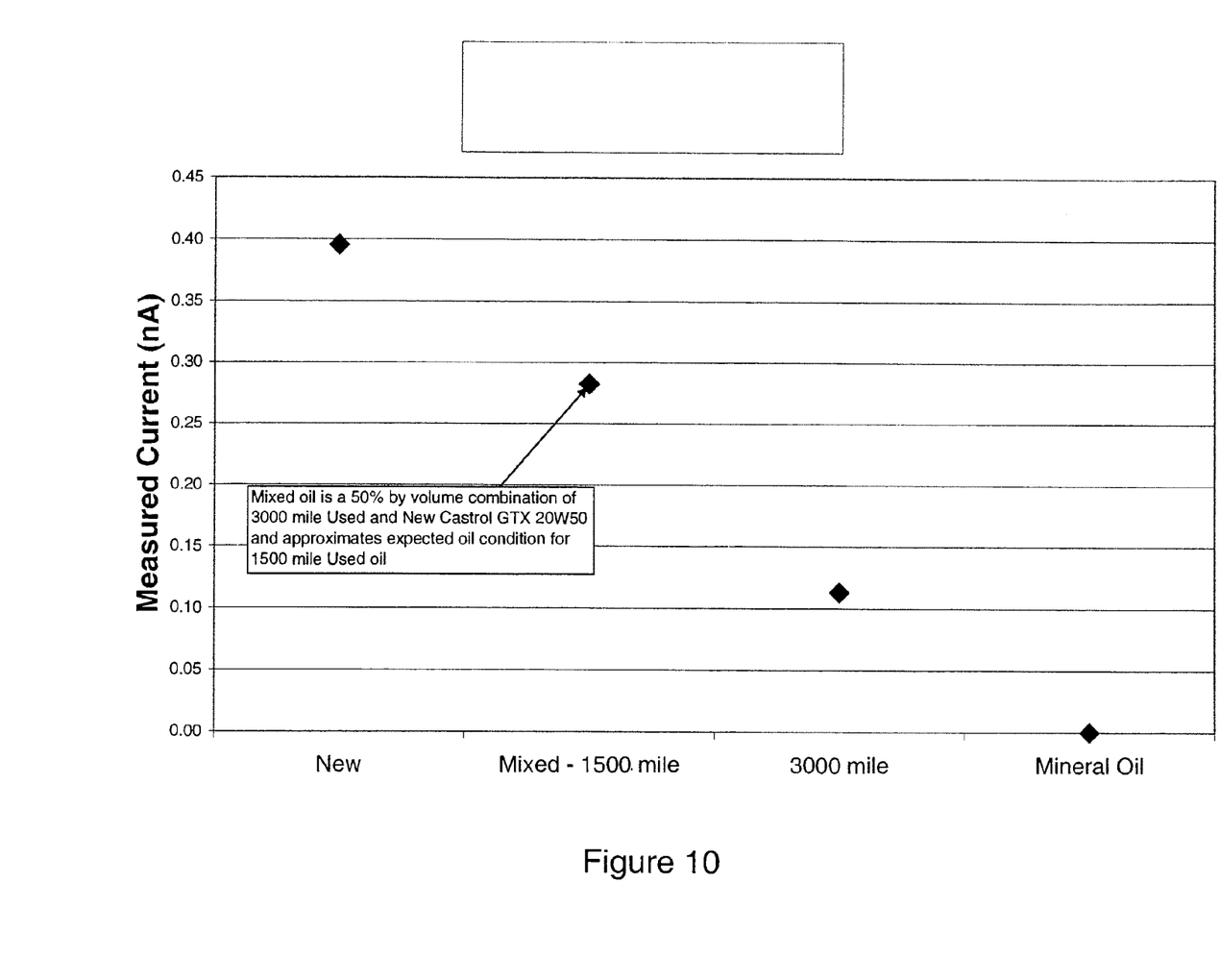
FIG. 10 illustrates measured sensor data for new and used lubricating motor (Castrol®, a registered trademark of Castrol Oil Co.) oil as well as a mixture of new and used lubricating motor oil and mineral oil.
Figure 11:
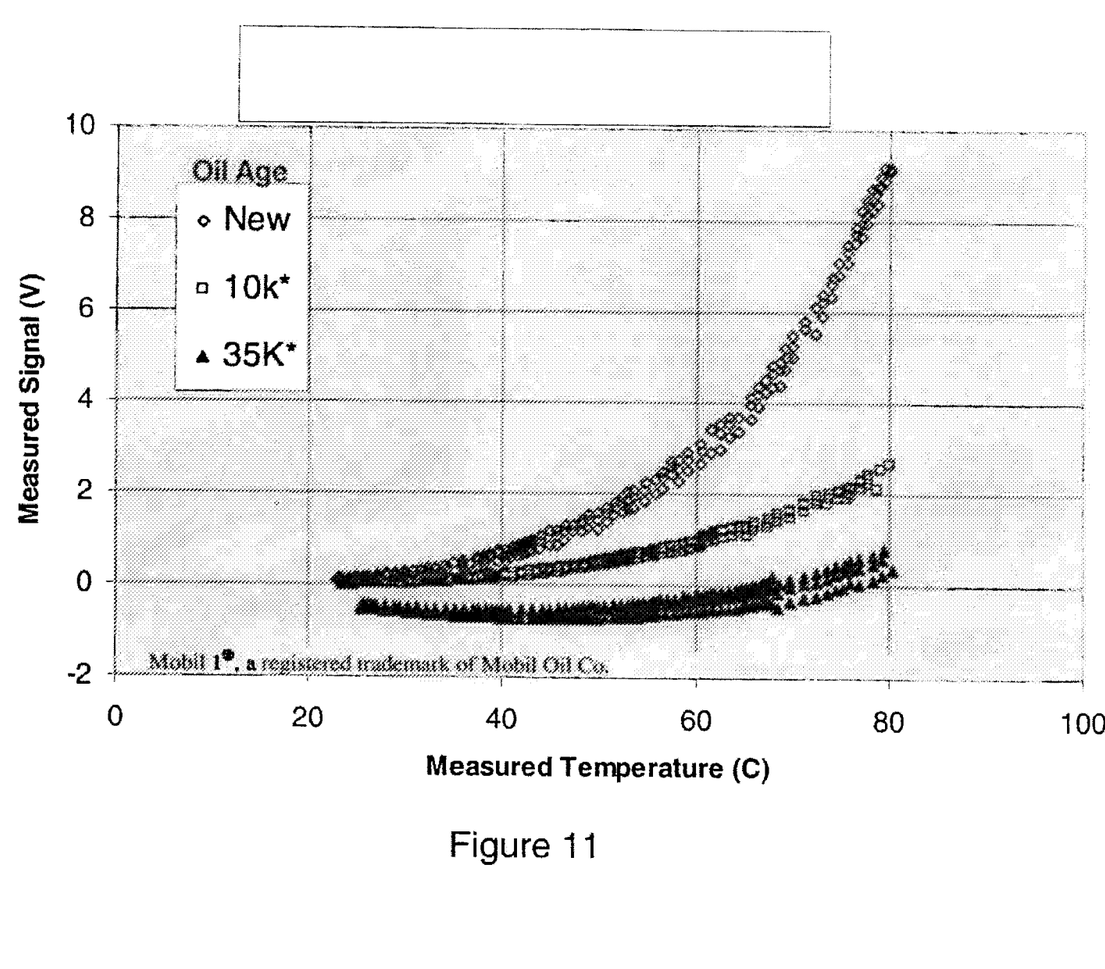
FIG. 11 illustrates measured sensor data for new and thermally aged lubricating motor oil as a function of temperature and equivalent miles driven after thermal aging (Mobil1®, a registered trademark of ExxonMobil Oil Co.)
Figure 12A:
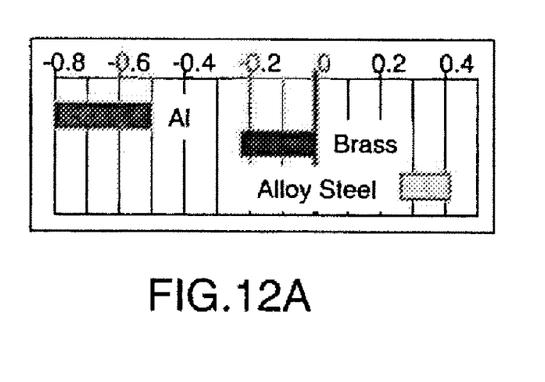
FIG. 12A shows commonly reported Galvanic potentials for metal pairs in sea water.
Figure 12B:
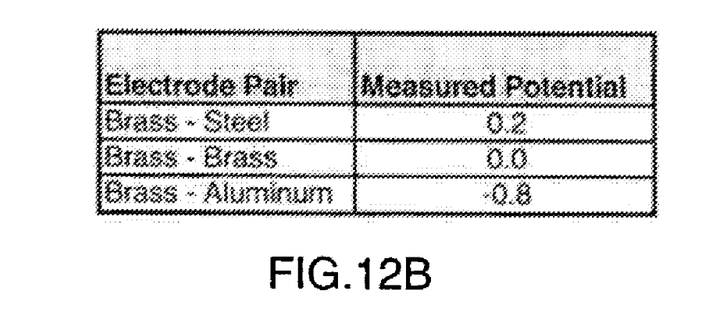
FIG. 12B shows tabulated sensor data for Galvanic potentials measured in oil using different metallic electrode pairs.
Figure 13:
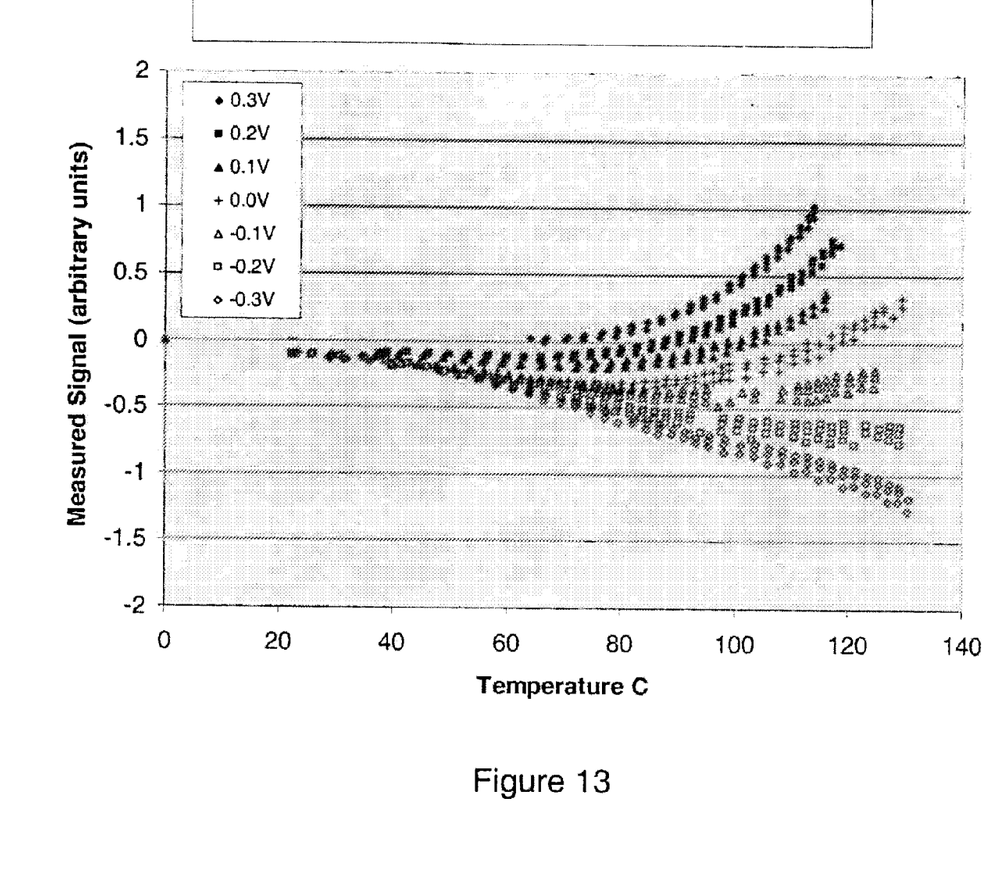
FIG. 13 illustrates measured data from amperometric sensors evaluating different applied voltage bias levels during measurement as a function of oil temperature (ROTELLA T®, a registered trademark of Shell Oil Co.)

A sensor 180 was constructed as shown in FIG. 8 (and used as shown in FIG. 9A) with the electrodes fashioned in the manner shown in FIGS. 6 and 7. The sensor 180 was used to evaluate a variety of mineral oils and lubricating motor oils. An analytical description of the measurement technique was set forth hereinbefore regarding FIGS. 9A-9C. Resulting measurements are set forth in FIGS. 10-13 and are well correlated and highly sensitive to changes in the fluid properties, as well as to the type of electrode pairs used to effectuate the measurements.

The foregoing description of embodiments of the present invention have been presented for purposes of illustration and description. It is not intended to be exhaustive or to limit the present invention to the precise form disclosed, and modifications and variations are possible in light of the above teachings or may be acquired from practice of the present invention. The embodiments were chosen and described in order to explain the principles of the present invention and its practical application to enable one skilled in the art to utilize the present invention in various embodiments, and with various modifications, as are suited to the particular use contemplated.

What is claimed is:

1. A method of determining chemical properties of a fluid, comprising the steps of:

placing a weak electrolytic hydrocarbon fluid into a fluid container;

disposing a detection device at least partly in the fluid container, the detection device including at least two electrodes;

coupling a detection and amplification device to the at least two electrodes, the at least two electrodes and the weak electrolytic hydrocarbon fluid collectively generating a galvanic electrical current sensible by the detection and amplification device; and measuring a change in composition of the weak electrolytic hydrocarbon fluid based on a change in the galvanic electrical current.

2. The method as defined in claim 1 further including the step of measuring corrosion currents by use of low impedance DC techniques.

3. The method as defined in claim 1 further including the step of applying low frequency voltage bias modulation to at least one of the at least two electrodes.

4. The method as defined in claim 1 further including the step of using closed-loop feedback to apply and measure electrical potential from the at least two electrodes.

5. The method of claim 1, wherein the weak electrolytic hydrocarbon fluid comprises an oil.

\* \* \* \* \*